United States Patent [19]

Heiland et al.

[11] 4,455,378

[45] Jun. 19, 1984

[54] METHOD OF DETERMINING THE CONTENT OF AN ANESTHETIC GAS IN A SELECTED LOCATION

[75] Inventors: Gerhard Heiland, Aachen; Heinz Laurs, Viersen, both of Fed. Rep. of Germany

[73] Assignee: Drägerwerk Aktiengesellschaft, Fed. Rep. of Germany

[21] Appl. No.: 372,048

[22] Filed: Apr. 26, 1982

[30] Foreign Application Priority Data

May 13, 1981 [DE] Fed. Rep. of Germany ....... 3118936

[51] Int. Cl.³ .............................................. G01N 27/12
[52] U.S. Cl. ...................................... 436/126; 422/98; 436/151
[58] Field of Search ........................ 436/124, 126, 151; 422/98, 88, 94–97

[56] References Cited

U.S. PATENT DOCUMENTS

| | | | |
|---|---|---|---|
| 3,961,248 | 6/1976 | Kawamura | 422/97 X |
| 3,999,122 | 12/1976 | Winstel et al. | 422/98 X |
| 4,039,941 | 8/1977 | Morrison | 422/98 X |
| 4,350,660 | 9/1982 | Robinson et al. | 422/98 X |
| 4,381,922 | 5/1983 | Frey et al. | 422/98 |

FOREIGN PATENT DOCUMENTS 2002907 2/1979 United Kingdom ................ 422/98

Primary Examiner—Arnold Turk
Attorney, Agent, or Firm—McGlew and Tuttle

[57] ABSTRACT

An apparatus for and method of determining the content of an anesthetic gas in a selected location is disclosed which comprises heating a sensor layer containing phthalocyanine, measuring the resistance of the sensor while it is heated, and selectively determining the content of the anesthetic gas either by measuring the variation of the electrical resistance or the rate of the variation of the electrical resistance. A device for carrying out the method comprises a carrier with a layer of copper phthalocyanine thereon is provided with electrical terminals for connection to a electrical current source. The sensor carried on a heatable carrier and an electrically heatable catalyst is arranged in the free space directly adjacent the sensor for dissociating the molecules of the anesthetic gas to be detected. The temperature of the catalyst is maintained higher than the temperature of the sensor layer and advantageously comprises a wire of metal from the series of the platinum metals. The carrier advantageously has a hot layer on one side and a contacted sensor layer on the opposite side. The sensor may be designed as a sandwich cell wherein the sensor layer is supplied on an electrode covered with a gas permeable cover electrode. The sensor layer advantageously comprises a precious metal. It is connected to a constant voltage source and the variation of current intensity is used as a measuring quantity of the resistance variation. It is advantageously constructed as a portable pocket device which can be connected with an accessory part for regenerating the sensor layer by increased heating which is advantageously produced by a supply of current to the layer.

7 Claims, 6 Drawing Figures

METHOD OF DETERMINING THE CONTENT OF AN ANESTHETIC GAS IN A SELECTED LOCATION

FIELD AND BACKGROUND OF THE INVENTION

The invention relates in general to gas detectors and in particular to a new and useful apparatus and method for measuring gaseous or vaporous media, where the variation or the rate of variation of the electrical resistance in a heated phthalocyanine containing sensor layer is used as a measuring quantity.

From German OS No. 28 09 873 is known a method for determining gaseous or vaporous media contained in the air, where the variation of the electrical resistance of a semiconductor selected from the series of the porphyrines, particularly phthalocyanine, is determined as a measuring quantity. The phthalocyanines can contain a metallic element, e.g. iron, nickel, cobalt, copper or manganese. As a sensor is used a coated contacted ceramic carrier which is connected to a device for measuring the resistance. As a resistance blank value of a sensor consisting of copper-phthalocyanine is indicated a value of $1.5 \times 10^6$ ohm. The absorbed gases lead to a reduction of the resistance, whereby the differential of the variation is used as a measuring quantity. The absorbed gases can be desorbed again by heat treatment. There is no mention of the usability for detecting anesthetic gases in room air in the ppm-range. Besides, the sensitivity of the above described sensor is much too low for such a test.

British Pat. A No. 20 02 907 provided a semiconductor oxide film as a gas sensor, which is specifically suitable for detecting combustible and reducing gases and vapors, but not for anesthetic gases. The semiconductor layer is covered by an aluminum oxide film which carries a catalyst layer. The known embodiment permits no temperature differences between the semi-conductive oxide film and the catalyst layer.

German Pat. No. 1,271,430 and AS No. 1,299,141 describe devices for the continuous determination of the content of organic anesthetic vapors in the breathing gas of a patient, where the portion of the anesthetic causes an elongation of a strip of swelling silicone rubber, which is evaluated to indicate the measuring quantity. But these devices make it possible only to indicate the relatively high portion of the anesthetic gas in the breathing gas of a patient (about 1%) but not the concentration of this anesthetic gas in the ambient room air, which is by several orders of magnitude lower. As admissible is considered here a limiting value of only 2 ppm.

The state of the art also comprises the EMMA apparatus, described in the EMMA brochure of June 1980 by Engstroem Medical AG, which measures individual anesthetic gases, like halothane, enflurane, methoxyflurane and isoflurane. An oscillating quartz coated with silicon oil as a sensor is used. The gas absorption of the oil layer results in a frequency variation of the oscillating quartz, which can be determined in an electrical circuit as a measure of the anesthetic gas portion. The apparatus is only suitable for monitoring a relatively high anesthetic gas portion in the breathing gas of the patient, its sensitivity does not suffice to monitor the much lower room air portions.

For measuring the anesthetic gas halothane in the room air is known a testing method described in German AS No. 2,830,781 where a color change appears above a given limiting value in the test tube turned to pyrolytically obtained free halogen. The test tube permits monitoring of the room air portion of halothane by random tests with a relatively high sensitivity in the range of 1 ppm.

SUMMARY OF THE INVENTION

The invention permits a sensitive measurement of an anesthetic gas portion in the room air with very simple means, where the dose acting within a certain time on the persons in the room can also be determined, if necessary. Another object of the invention is to provide a device for carrying out the measuring method by means of a safe, simple sensor, which is particularly sensitive to certain anesthetic gases.

The invention provides a measuring method for gaseous or vaporous media, where the variation or the rate of variation of the electrical resistance of a heated phthalocyanine containing sensor layer is used as a measuring quantity to determine the content of anesthetic gases, consisting of halogenated organic compounds in the room air. The measuring method can preferably be carried out with a metal free phthalocyanine or a metal phthalocyanine containing sensor layer. It is advisable to use a sensor layer containing copper phthalocyanine. The anesthetic gases halothane, enfluorane and forane can be effectively detected. The high sensitivity of the measuring method specifically for anesthetic gases comprising halogenated compounds is particularly surprising. The above described sensor permits detection of anesthetic gas portions of halogen of the order of 1 ppm. About the same sensitivity is also indicated for the anesthetic gases enflurane and forane. But the sensitivity to nitrous oxide $N_2O$, acetone and ethyl alcohol is much lower. Detectable signals appear only at above 10,000 ppm. The dose of the anesthetic gases absorbed from the room air can be preferably determined by determining the resistance value of the sensor layer. This resistance value drops rapidly under the action of the anesthetic gas and rises only relatively slowly again at room temperature without additional regenerative heating. There is an integrating effect, and it is possible to manufacture stationary or portable devices which indicate the dose at the end of the observation period of up to 12 hours and/or which release a corresponding warning signal. Subsequently the sensor coat is regenerated again by heating to 50° to 100° C.

A sensitive sensor can be so designed that a heatable catalyst for dissociating the molecules of the anesthetic gas to be detected is arranged in the range of the phthalocyanine containing sensor layer provided on a heatable carrier in the free air space in front of the sensor layer. The temperature of the catalyst is preferably much higher than the temperature of the sensor layer and is between 200° and 600° C. with advantage, while the temperature of the sensor layer is just above room temperature, about 20° to 40° C. Due to the different heating of sensor layer and catalyst, it is possible to considerably increase the detection sensitivity.

The catalyst is preferably a wire, particularly wire coil, of a metal from the series of the platinum metals, preferably a palladium or platinum. A first short wire suffices for the desired effect.

An advantageous arrangement can be so selected that the sensor comprises a plate-shaped ceramic carrier, provided on one side with a hot layer, while the other side is provided with the contacted sensor layer. In an alternate, perhaps more expedient embodiment, the sensor comprises a sandwich cell, where the sensor layer is applied on a metal electrode and covered with a gas-permeable counter-electrode. The gas permeability of the counter electrode can be achieved in various ways, e.g. by a sufficiently low coat thickness or by perforation.

It seems particularly important that the contacts of the sensor layer consists of a precious metal, because the great work function of the precious metal increases the desired effect.

From an electrical point of view it seems to be of advantage to apply to the sensor layer a constant d-c voltage of a few Volts, and to use the resulting current intensity variation as a measuring quantity of the resistance variation. In a wide range, the rate of variation is proportional to the concentration of the anesthetic gas in the room.

In the portable design as a pocket device, it may be of advantage that an accessory part is provided for regenerating the sensor layer by increased heating, with which the pocket device can be connected, e.g. by plugging, and which has a current supply for the increased heating of the sensing layer, where the corresponding contact connections are automatically established during the plugging.

Accordingly, it is an object of the invention to provide an improved method of determining the content of an anesthetic gas in a selected location which comprises heating a sensor layer containing phthalocyanine in the selected location and selectively determining the output of the anesthetic gas by measuring at least one of the variation of the electrical resistance and the rate of variation of the electrical resistance.

A further object of the invention is to provide a device for use determining an anesthetic gas in a certain area which comprises a carrier, a sensor layer of copper phthalocyanine disposed on said carrier, electrode means connected to said sensor layer and an electrically heatable catalyst disposed adjacent said sensor layer.

A further object of the invention is to provide a device for measuring the presence of an anesthetic in a selected area which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
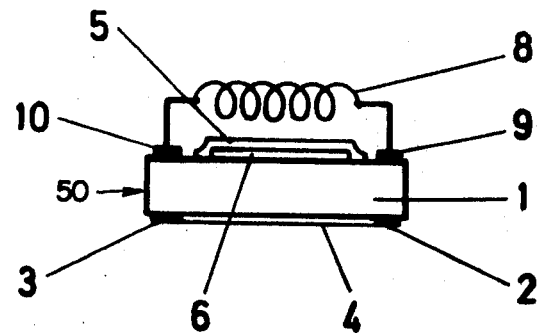
FIG. 1 is a side elevational view of a sensor constructed in according with the invention.
Figure 2:
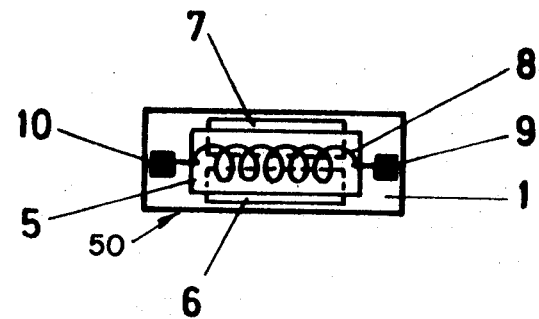
FIG. 2 is a top plan view of the sensor shown in FIG. 1.

Referring to the drawings, in particular the invention embodied therein in FIGS. 1 and 2, comprises a device for measuring the content of an anesthetic gas in a selected atmosphere which comprises a transportable heatable carrier 1 with a sensor layer 5 thereon of copper phthalocyanine and designated 5. The sensor layer 5 is arranged adjacent an electrically heatable catalyst 8 which extends in a free space over the sensor layer for dissociating the molecules of the anesthetic gas to be detected. The temperature of the catalyst is advantageously maintained higher than the temperature of the sensor layer 5. The temperature of the catalyst for example may be from 200° to 600° C. and the temperature of the sensor layer 5 about 20° to 40° C. The catalyst 8 advantageously comprises wire metal from the series of the platinum metals. The plate shaped ceramic carrier 1 is advantageously provided on one side with a hot layer 4 and on the other side with the contacted sensor layer 5. The sensor 5 may be designed as a sandwich cell applied on an electrode 6 and covered with a gas permeable cover electrode 7. The sensor layer is connected to a constant voltage source and the variation of the current intensity is measured and used as a measuring quantity of the resistance variation. The sensor is advantageously constructed as a portable pocket device and can be connected with an accessory part (not shown) for regenerating the sensor layer by increased heating. The accessory part which is not shown, for example, would have a current supply for the increased heating of the sensor layer.

In the sensor 50 shown in FIGS. 1 and 2, designed as an area cell, a ceramic carrier 1 is provided, e.g. of aluminum oxide, has on its underside a semi-conducting hot layer 4 provided with respective terminals or contact elements 2 and 3. On the surface of ceramic carrier 1 is provided a sensor layer 5 containing copper phthalocyanine (CuPc), which is contacted with vapor deposited connecting electrodes 6,7 of gold on an adhesion improving chromium layer. In the free air space about 10 mm in front of or over sensor layer 5, is arranged a heatable platinum wire coil 8 serving as a catalyst, which are connected with respective connecting terminals or contacts 9 and 10.

Figure 3:
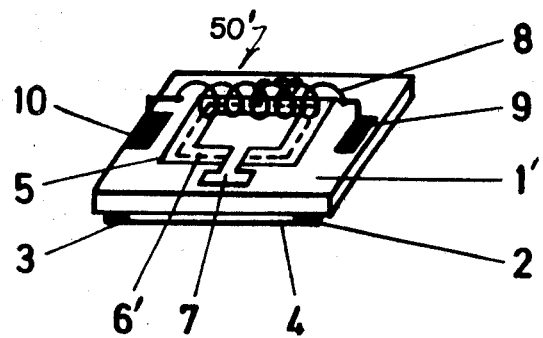
FIG. 3 is a perspective view of another embodiment of the sensor designed as a sandwich cell.

In the embodiment of the sensor 50' as a sandwich cell according to FIG. 3, one connecting electrode 6' is arranged on the topside of ceramic carrier 1. It carries the sensor layer 5, which is covered at the top with the gas permeable connecting electrode 7 as a counter electrode. In the free air space in front of connecting electrode 7 and sensor layer 5 is arranged the catalyst in the form of a wire coil 8 with terminal contacts 9 and 10. On the underside of a ceramic carrier 1' is the semiconducting hot layer 4 provided with contact elements 2 and 3. Connecting electrodes 6' and 7 consist of gold (Au).

Figure 4:
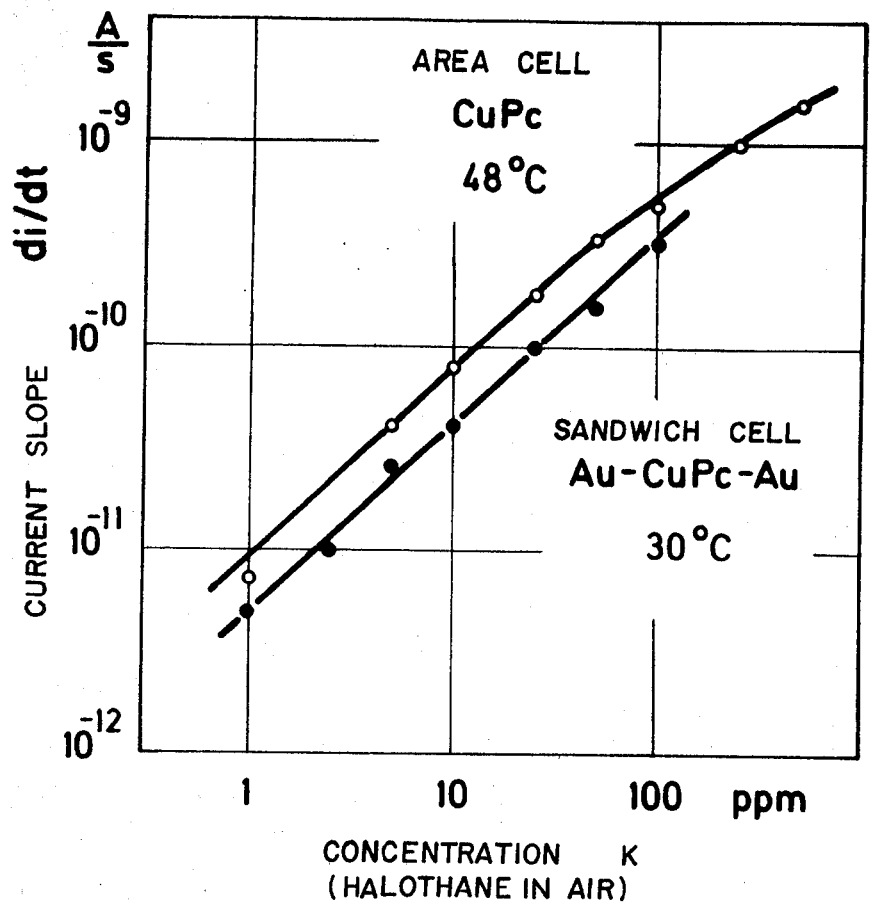
FIG. 4 is a diagram indicating the current slope as a function of the concentration of an area cell and a sandwich cell with the anesthetic gas.

FIG. 4 compares an area cell CuPc and a sandwich cell Au-CuPc-Au regarding the current slope as a measuring quantity corresponding to the variation of the concentration K of the anesthetic gas to be detected. It was found that the rate of variation is in a wide range proportional to the concentration of the anesthetic gas.

Figure 5:
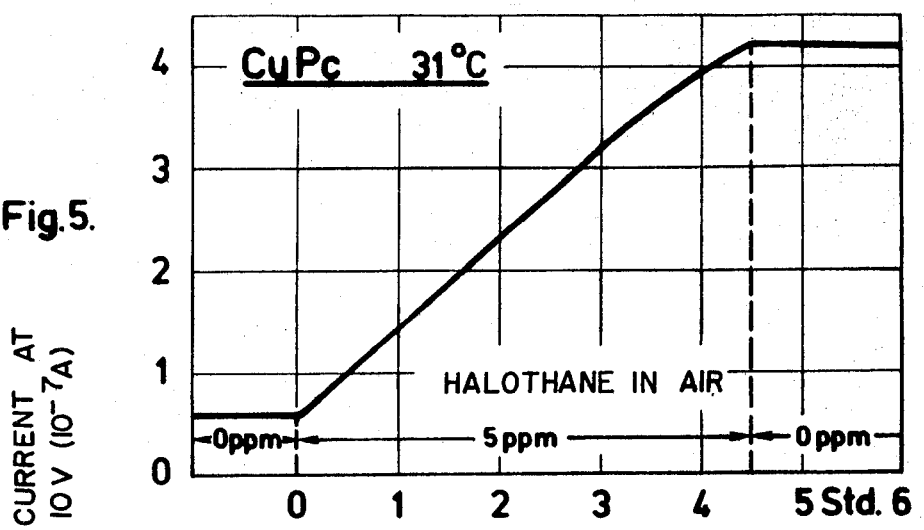
FIG. 5 is a diagram showing the integrating function in a sensor designed as an area cell.
Figure 6:
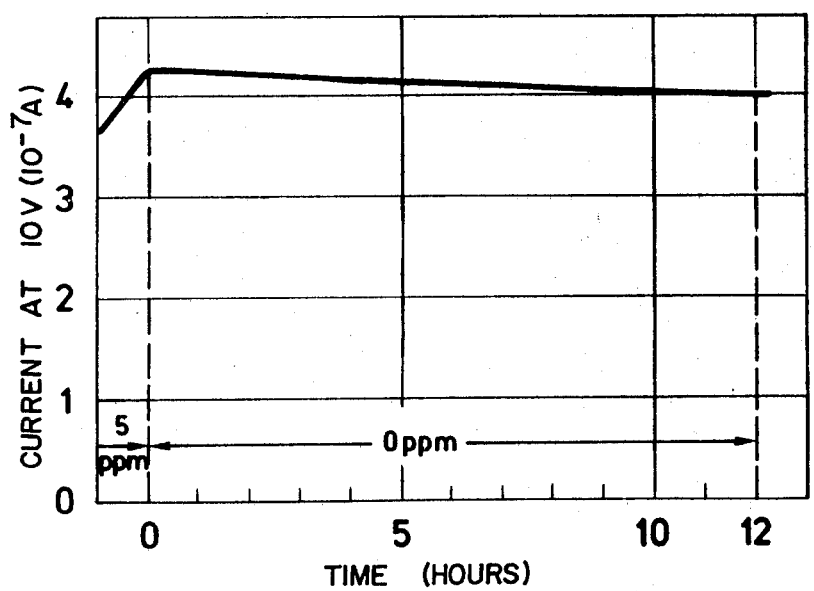
FIG. 6 is a diagram the decrease of the stored measuring value in the sensor represented in FIG. 5.

The representation in FIGS. 5 and 6 shows the usefulness of the sensor as an integrating element for the determination of the dose. As it can be seen from FIG. 5, a constant action of 5 ppm halothane leads within 4½ hours to a current rise from $0.6 \times 10^{-7}$ A to $4.3 \times 10^{-7}$ A. FIG. 6 shows that the current intensity attained decreases very slowly within 14 hours at elevated room temperature of 31° C., in the present case only by about 6%.

The temperature data concerns the heating of the sensor layer, which is preferably set to the desired value by a corresponding control circuit.

While specific embodiments of the invention have been shown and described in detail to illustrate the application of the principles of the invention, it will be understood that the invention may be embodied otherwise without departing from such principles.

What is claimed is:

1. A method of determining the content of an anesthetic gas containing at least one of the group consisting of halothane, enflurane and forane in a selected atmosphere, comprising heating a sensor layer which contains phthalocyanine and is in the selected atmosphere, dissociating the anesthetic gas by a heatable catalyst in a free space in front of the sensor layer, measuring the resistance of the sensor layer while it is heated, and selectively determining the content of the anesthetic gas by measuring at least one of the variation of electrical resistance and the rate of variation of electrical resistance.

2. A method according to claim 1, wherein the sensor layer contains metal-free phthalocyanine.

3. A method according to claim 1, wherein the resistance value of the sensor layer is measured after a duration of exposure of the sensor layer to the gas in the selected atmosphere for determining a total dosage of gas accepted from the free space by the sensor layer.

4. A method according to claim 1, wherein the sensor layer contains a metal phthalocyanine.

5. A method according to claim 4, wherein said metal phthalocynine is copper phthalocyanine.

6. A method according to claim 1, wherein the catalyst is maintained at a temperature higher than the sensor layer.

7. A method according to claim 6, wherein the temperature of the catalyst is maintained at from 200° to 600° C. and the temperature of the sensor layer is maintained at from 20° to 40° C.

* * * * *